(12) United States Patent
Chen

(10) Patent No.: US 6,511,440 B2
(45) Date of Patent: Jan. 28, 2003

(54) SAFETY VACUUM SYRINGE FOR BLOOD SAMPLING CONFORMED TO ERGONOMICS

(76) Inventor: Long Hsiung Chen, 4F, No. 29, Lane 286, Shih Tung Rd., Shih Lin Dist., Taipei (TW)

( * ) Notice: Subject to any disclaimer, the term of this patent is extended or adjusted under 35 U.S.C. 154(b) by 5 days.

(21) Appl. No.: 09/765,356

(22) Filed: Jan. 22, 2001

(65) Prior Publication Data

US 2002/0099355 A1 Jul. 25, 2002

(51) Int. Cl.[7] .................................................. A61B 5/00
(52) U.S. Cl. ........................ 600/576; 600/577; 604/195
(58) Field of Search ................................ 604/195, 263, 604/110, 187, 197, 576, 577, 573

(56) References Cited

U.S. PATENT DOCUMENTS

| | | | | |
|---|---|---|---|---|
| 3,326,206 A | * | 6/1967 | Barr, Sr. et al. | |
| 3,434,468 A | * | 3/1969 | Barr, Sr. et al. | |
| 3,520,292 A | * | 7/1970 | Barr, Sr. et al. | 604/197 |
| 3,822,701 A | * | 7/1974 | Cloyd | |
| 4,844,089 A | * | 7/1989 | Roberti | |
| 5,070,885 A | * | 12/1991 | Bonaldo | |
| 5,637,092 A | * | 6/1997 | Shaw | 604/110 |
| 6,102,894 A | * | 8/2000 | Dysarz | 604/110 |
| 6,152,901 A | * | 11/2000 | Arruego et al. | 604/195 |

* cited by examiner

Primary Examiner—Steven O. Douglas
Assistant Examiner—Khoa Huynh
(74) Attorney, Agent, or Firm—Rosenberg, Klein & Lee

(57) ABSTRACT

An ergonomic safety vacuum syringe for sampling blood includes a hollow barrel, a reduced lining tube and a vacuum tube. The barrel has a reduced inlet disposed on the top end thereof and a guiding slit disposed at a flank side. The reduced lining tube is installed in the barrel and includes an eccentric reduced portion disposed on the top end of the reduced lining tube and has an opening at the lower end. A needle head is engaged on the eccentric reduced portion and a through guiding hole is disposed at the center of the eccentric reduced portion to position a reverse Z-shaped needle therein, a lower needle tip of the needle is positioned at a central axis in the reduced lining tube, a press plate is positioned in the guiding slit. The vacuum tube is disposed in the barrel, and contains an elastic plug that is covered on an opening at the upper side of the vacuum tube.

7 Claims, 15 Drawing Sheets

SAFETY VACUUM SYRINGE FOR BLOOD SAMPLING CONFORMED TO ERGONOMICS

FIELD OF THE INVENTION

The present invention relates to a safety vacuum syringe for blood sampling conformed to ergonomics, and more particularly to the syringe that not only conforms to ergonomics in use but may receive the conventional needle head and the vacuum tube so as to lower production cost.

BACKGROUND OF THE INVENTION

Many viruses and diseases or bodily functions can be examined by a blood test, which makes blood testing to be a regular and frequent job. In preventing a patient from infecting health care workers with a lethal virus or germ, the selection of a blood sampling tool will be very important during a blood sampling process. Therefore, in order to make blood sampling safer, blood sampling must have some degree of improvement.

The needle head of a conventional blood sampling syringe, as revealed in U.S. Pat. No. 5,423,758, is disposed at the central axis of the front end of the syringe. During a blood sampling process, a needle of a syringe is stuck into a patient's vein to draw blood from the vein. The angle between the syringe and the skin surface of a human body is large when blood sampling is processed because the needle head is at the center of the syringe. Also, the needle head is difficult to be inserted into the vein to draw blood. This is especially true for patients whose blood vessels are thinner because it is easier for the needle to pass through the blood vessel. Thus, blood sampling cannot be performed smoothly.

SUMMARY OF THE INVENTION

One objective of the present invention is to provide a safety vacuum syringe for blood sampling conformed to ergonomics, whereby a needle head is eccentrically disposed at the front end of a syringe to lower the blood sampling angle during the blood sampling process allowing blood sampling to be performed more smoothly.

Another objective of the present invention is to provide a safety vacuum syringe for blood sampling, whereby an inner needle tip of the needle head has a reverse Z-shape so that it can be positioned at the center of the needle head to fit the traditional vacuum blood collecting cup.

Still another objective of the present invention is to provide a conventional needle head that can be used according to a users' need.

BRIEF DESCRIPTION OF THE DRAWING

The present invention can be better understood by detailed description of the following drawings, in which.

DETAILED DESCRIPTIONS OF THE INVENTION

Figure 1:
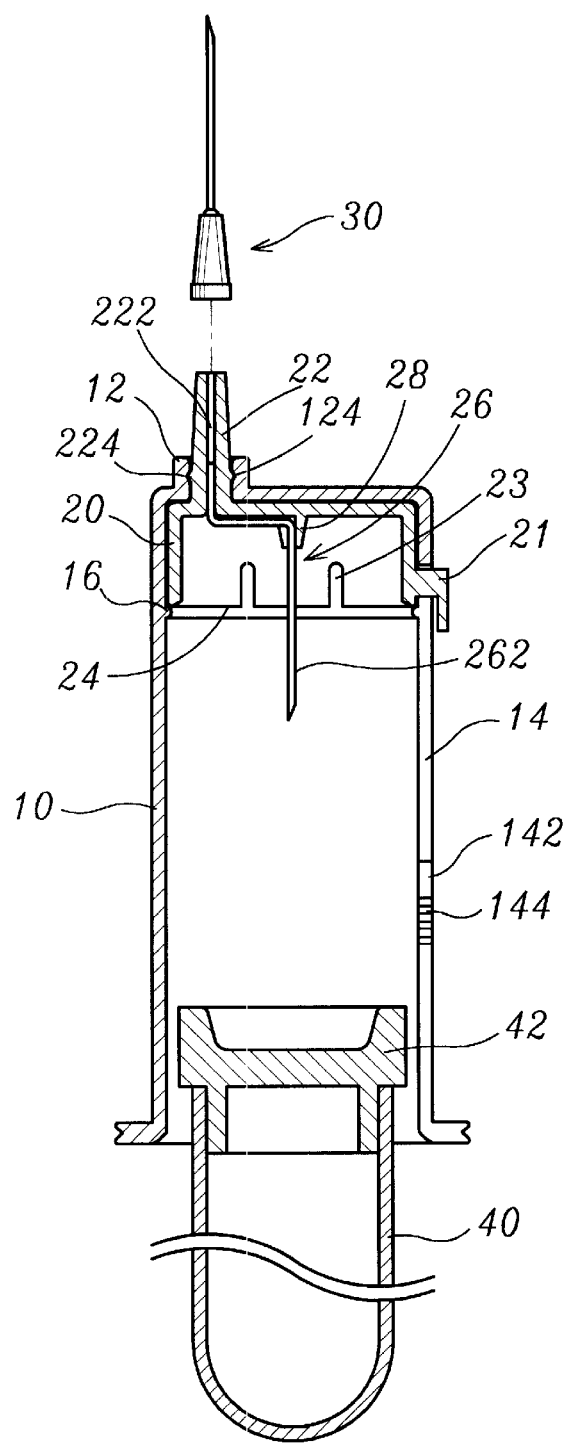
FIG. 1 is a longitudinal sectional view of a preferred embodiment of the present invention before a needle holder is mounted on a syringe.
Figure 2:
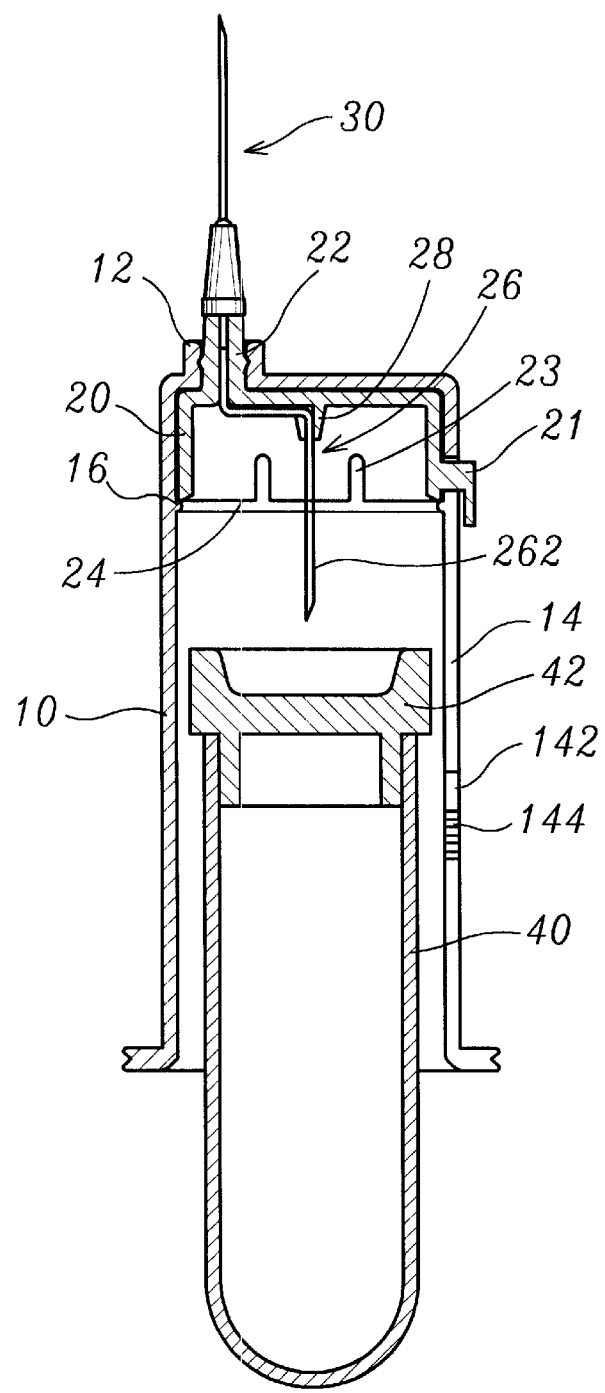
FIG. 2 is a longitudinal sectional view of a preferred embodiment of the present invention after a needle holder is mounted on a syringe.
Figure 3:
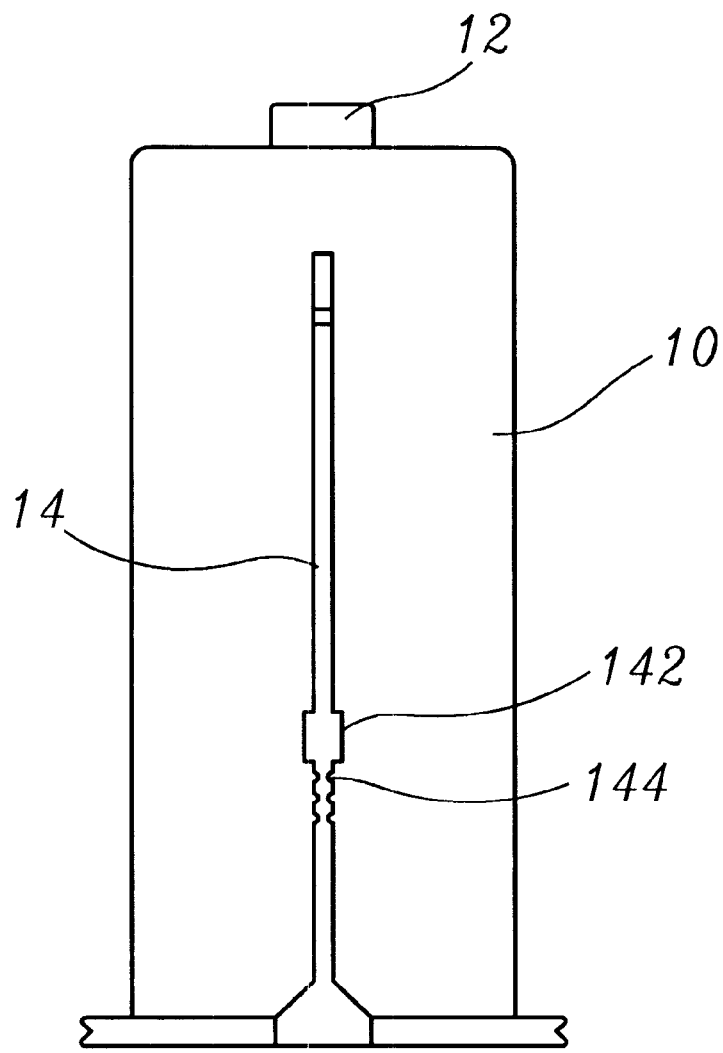
FIG. 3 is a side view of a preferred embodiment of the present invention, showing a guide groove.
Figure 5:
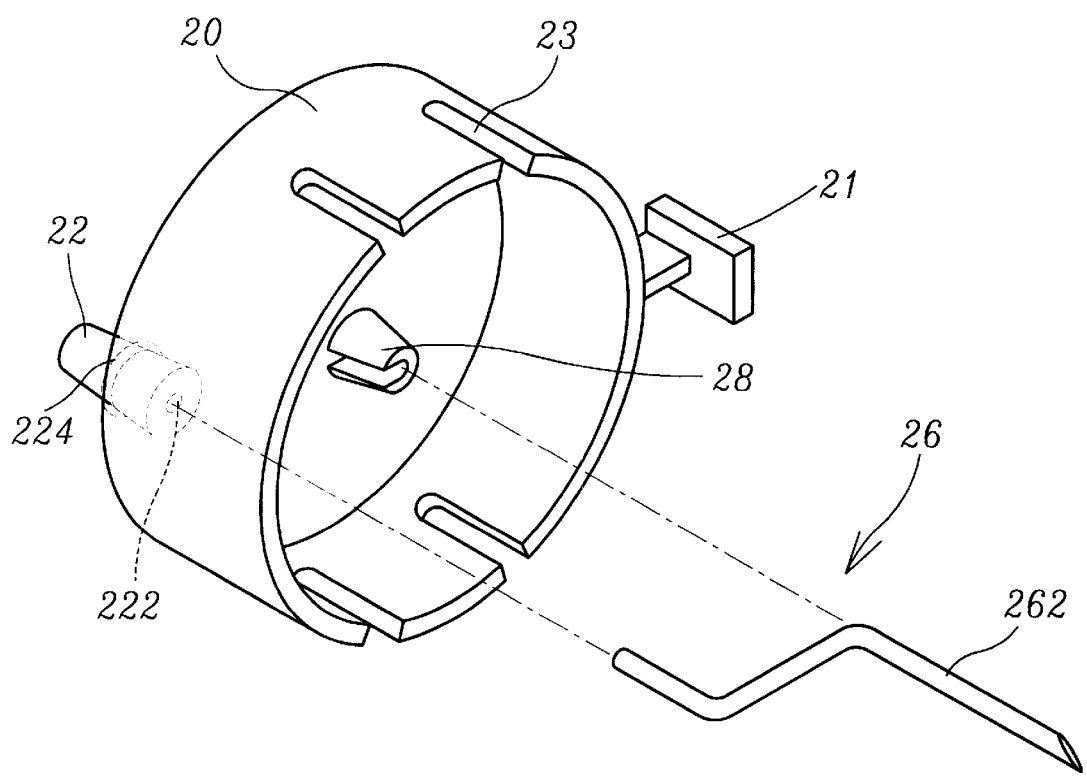
FIG. 5 is an explosive view of a reduced lining tube.

As shown in FIGS. 1, 2 and 3, the present invention comprises a hollow barrel 10, a reduced inlet 12 eccentrically disposed at the top end of the barrel 10 and a guide slit 14 at the flank side of the barrel 10. The barrel comprises a reduced lining tube 20, an eccentric reduced portion 22 is disposed at a position away from the center of the top end of the reduced lining tube 20 and an opening 24 formed at the bottom thereof. The eccentric reduced portion 22 can be embedded into the reduced inlet 12 and projects out of the reduced inlet 12. A needle head 30 can be wedged onto the eccentric reduced portion 22, and a through guiding hole 222 is disposed at the center of the eccentric reduced portion 22 so that a reverse Z-shaped type needle 26 can be fixed therein and a lower needle tip 262 of the needle 26 can be placed at the central axial line of the reduced lining tube 20. A fixing seat 28 is disposed at the center of the inner section of the reduced lining tube 20 for receiving and fixing the needle 26 therein. As shown in FIG. 5, a press plate 21 is further attached to the reduced lining tube 20 at the outer surface thereof and positioned in the guiding slit 14 to be utilized to drive the reduced lining tube to move in the longitudinal direction of the barrel 10.

A hook-shaped flange 16 is further disposed at a proper position of the inner surface of the barrel 10 so as to position the reduced lining tube 20 at the top end of the barrel 10 and not to slide loosely therein. Furthermore, at least one circular flange 224 is disposed around the eccentric reduced portion 22 and at least one circular groove 124 is disposed around the inner surface of the reduced inlet 12 to accommodate and position the circular groove 124. A plurality of small slits 23 are cut around lower side of the reduced lining tube 20, enabling the lower end of the reduced lining tube to maintain its proper elasticity. A vacuum tube 40 is further disposed inside the barrel 10, and an elastic plug 42 is fixedly covered in an opening that is at the top end of the vacuum tube 40. The vacuum tube 40 is commercially available.

Figure 6:
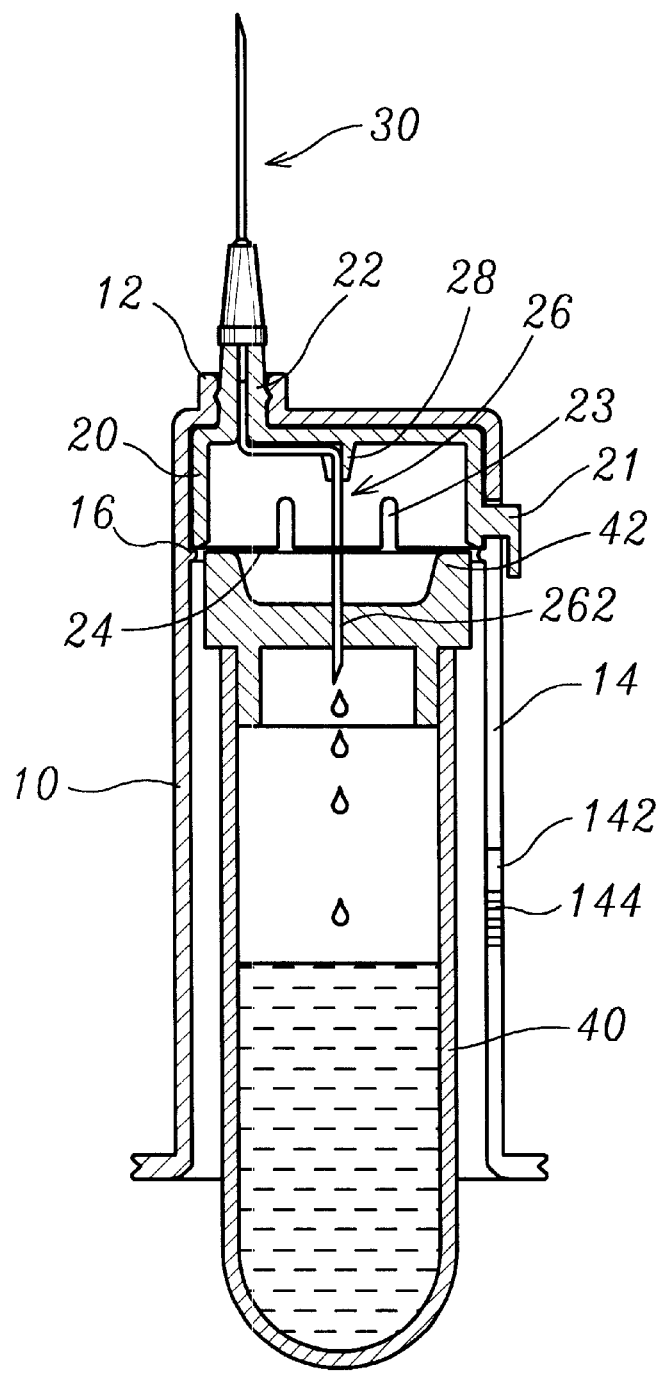
FIG. 6 is a longitudinal sectional view of a preferred embodiment of the present invention during use.

As shown in FIG. 6, when processing a blood sample, the needle head 30 is inserted into the vein of a patient, and the vacuum tube 40 moves toward the needle 26 inside the barrel 10 in order to force the lower needle tip 262 to prick through the plug 42 on the top of the cup 40. The blood from the vein of the patient will pass through the needle head 30, the guiding hole 222, the needle 26, and into the vacuum blood collecting cup 40. Since the needle head 30, the eccentric reduced portion 22 and reduced inlet 12 are all eccentrically disposed and close to the circumference of the barrel 10, a health care worker can prick the needle head 30 into the vein with a smaller inclined angle to the skin of the patient. Thus, the vacuum syringe for blood sampling not only conforms to ergonomics, but prevents the needle head from passing through the blood vessels.

Figure 4:
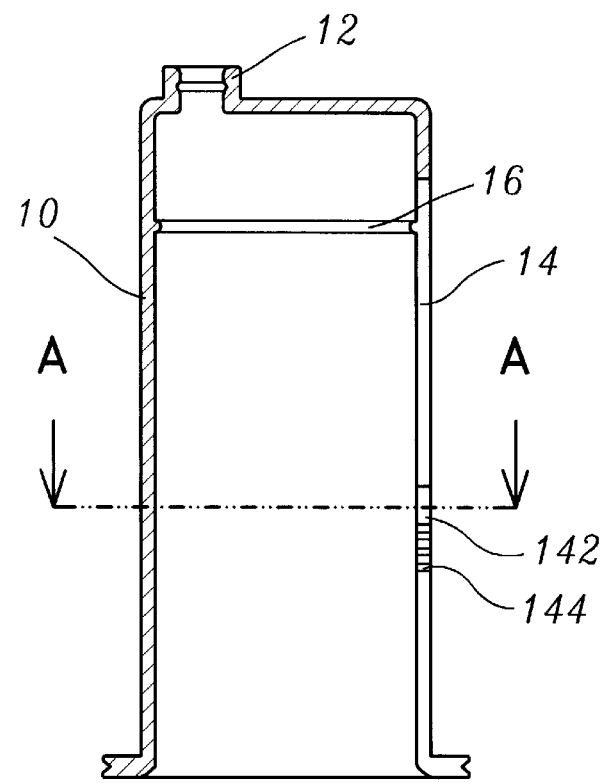
FIG. 4 is a longitudinal sectional view of a preferred embodiment of the present invention, showing the structure inside.
Figure 4A:
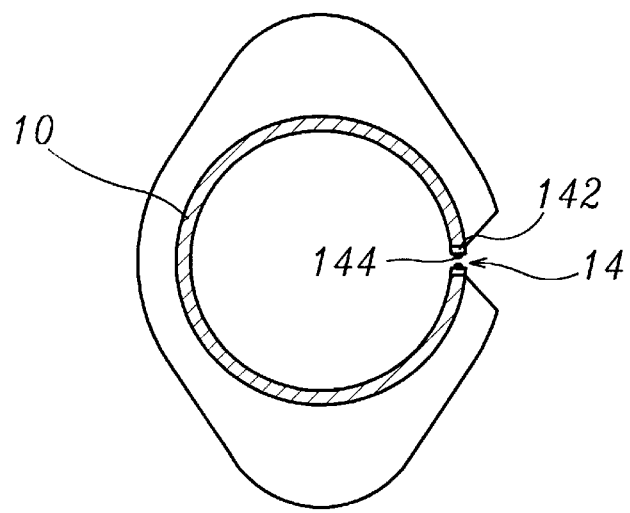
FIG. 4A is a sectional view of a preferred embodiment of the present invention when viewed along the section line A—A of FIG. 4.
Figure 7:
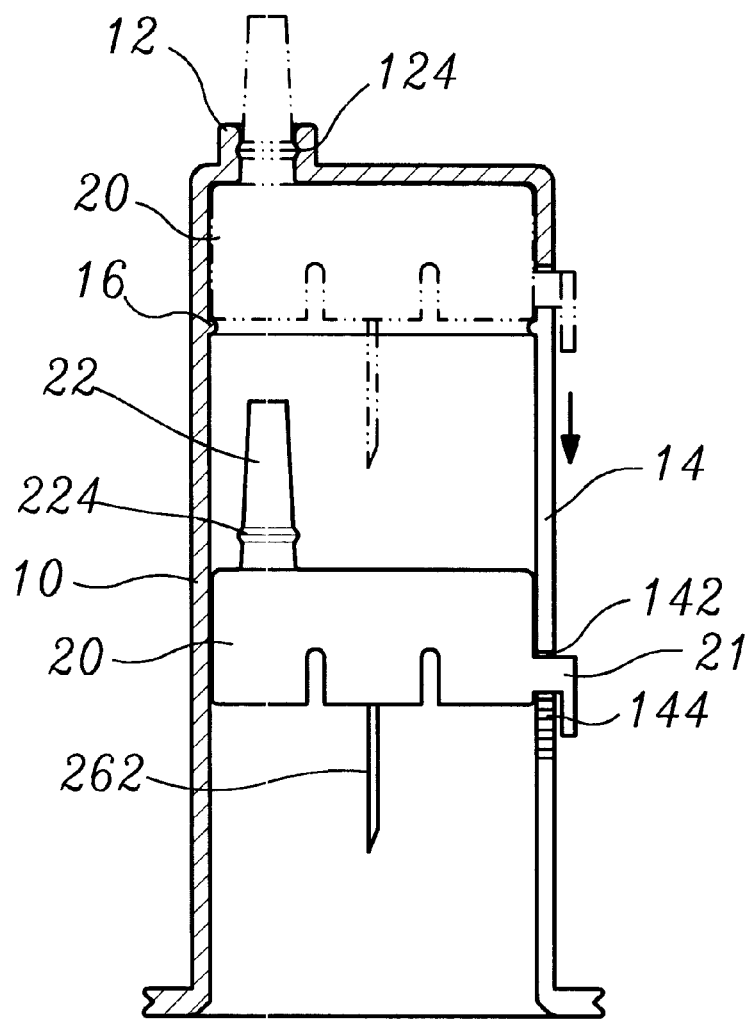
FIG. 7 is a longitudinal sectional view of a preferred embodiment of the present invention, showing a condition withdrawing a reduced lining tube back.

Referring to FIG. 7, after the blood sampling is over, the press plate 21 is pressed backward to move the reduced lining tube back to prevent the needle head from pricking the health care workers. A stopping groove 142 is disposed at a proper position of the guiding slit 14, the width of the stopping groove 142 is larger than the width of the guiding slit 14 in order to stop the press plate 21 from moving forward or backward when the press plate 21 is moved to the stopping groove 142 to avoid the lower needle tip 262 at the lower end of the needle 26 to project out of the barrel 10 to cause danger. A plurality of bulging points 144 are disposed at the section of the guiding slit 14 below the stopping groove 142 to prevent the press plate 21 from slipping backwards to drop out of the stopping groove 142 resulting in the lower needle tip being exposed from the barrel 10, as shown in FIGS. 4 and 4A.

Figure 8:
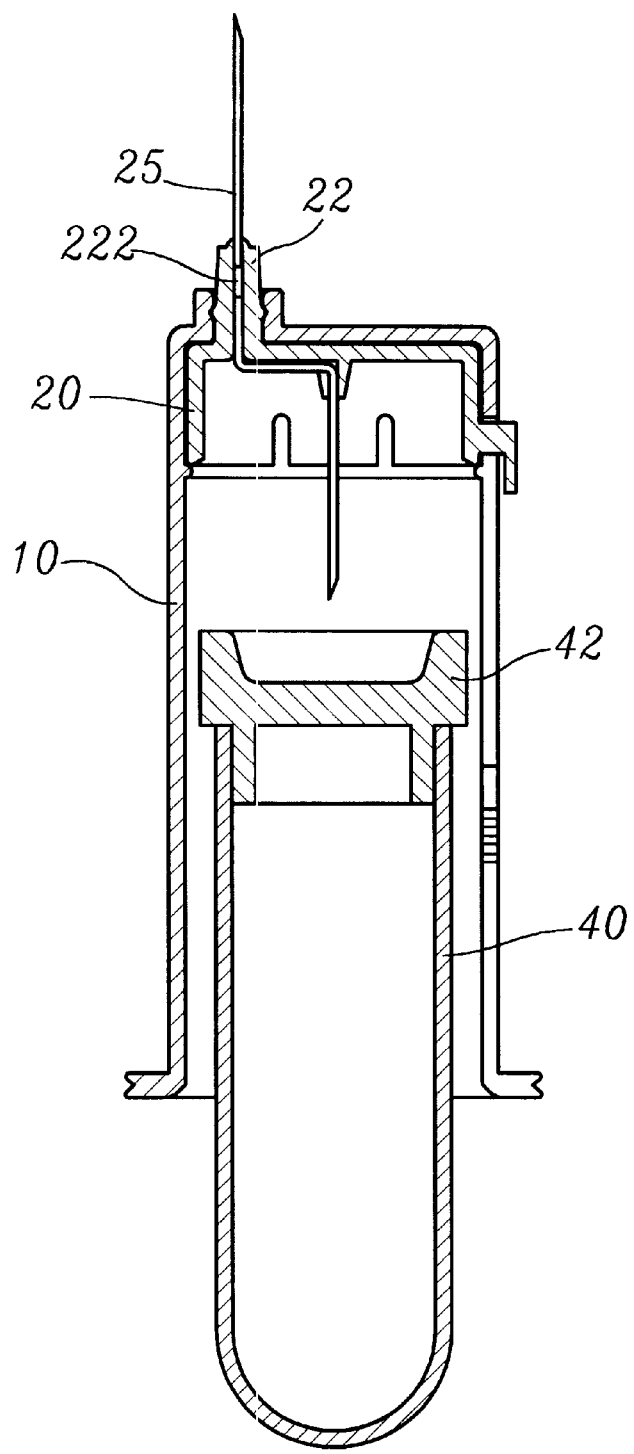
FIG. 8 is a longitudinal sectional view of a preferred embodiment of the present invention, showing a needle head being directly inserted into an eccentric reduced portion.
Figure 9:
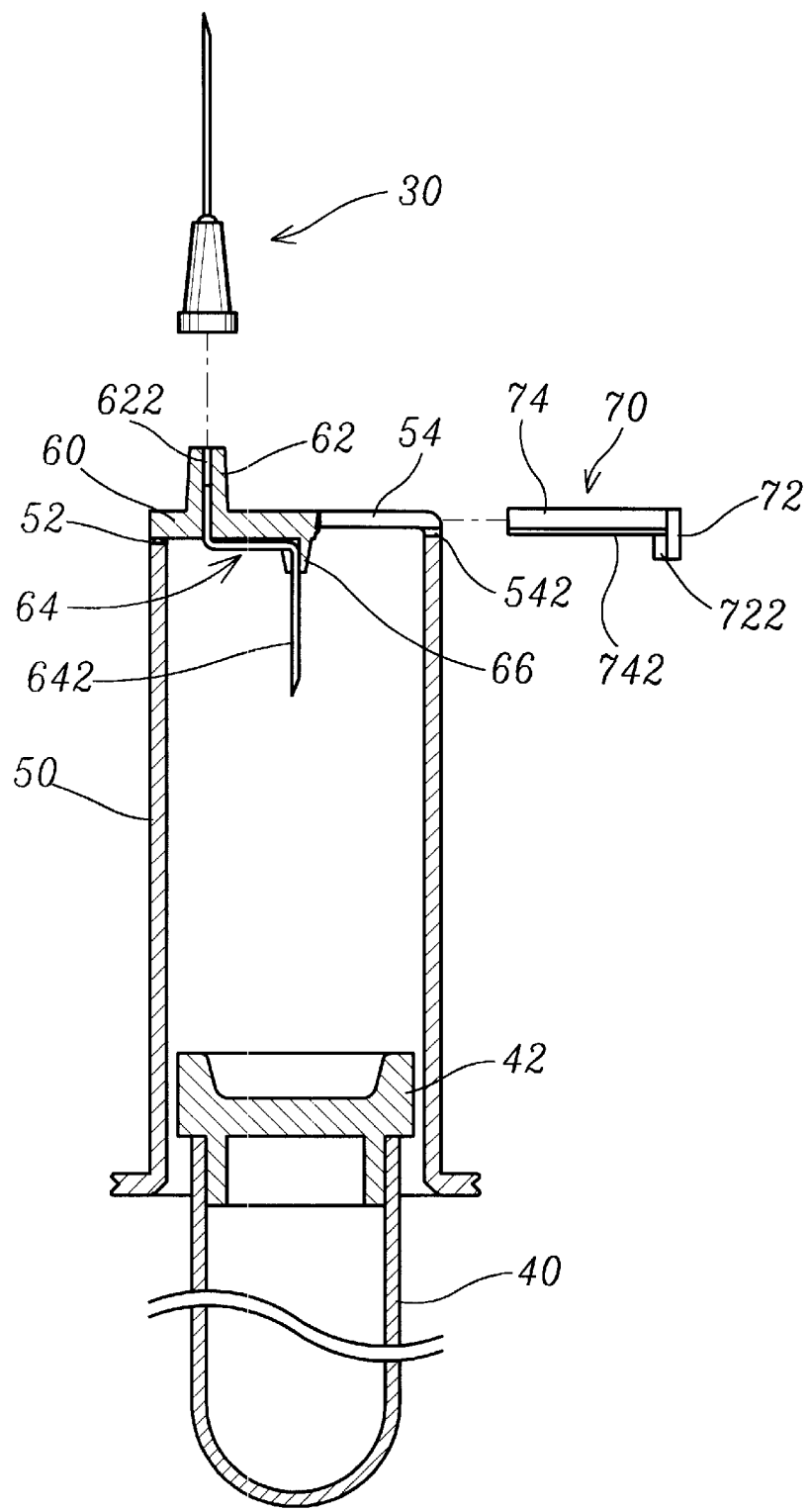
FIG. 9 is a longitudinal sectional view of another preferred embodiment of the present invention, showing a press plate being separated from a syringe.
Figure 10:
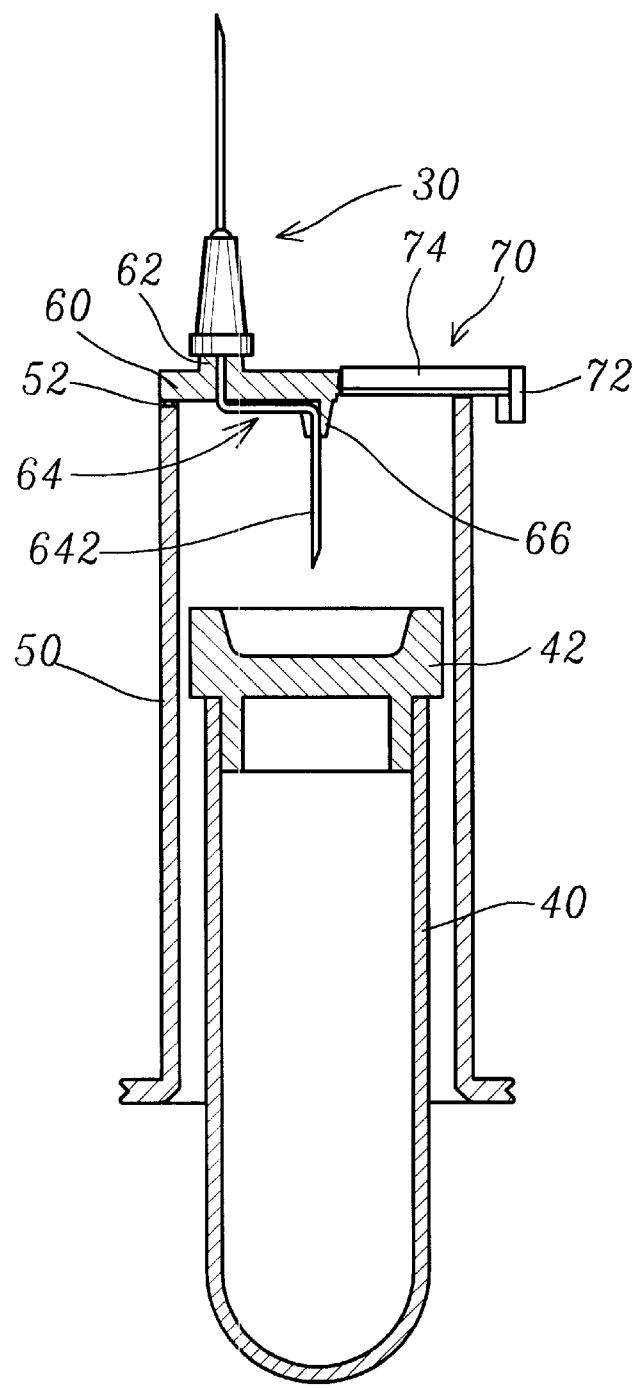
FIG. 10 is a longitudinal sectional view of another preferred embodiment of the present invention, showing a press plate being wedged into a syringe.
Figure 11:
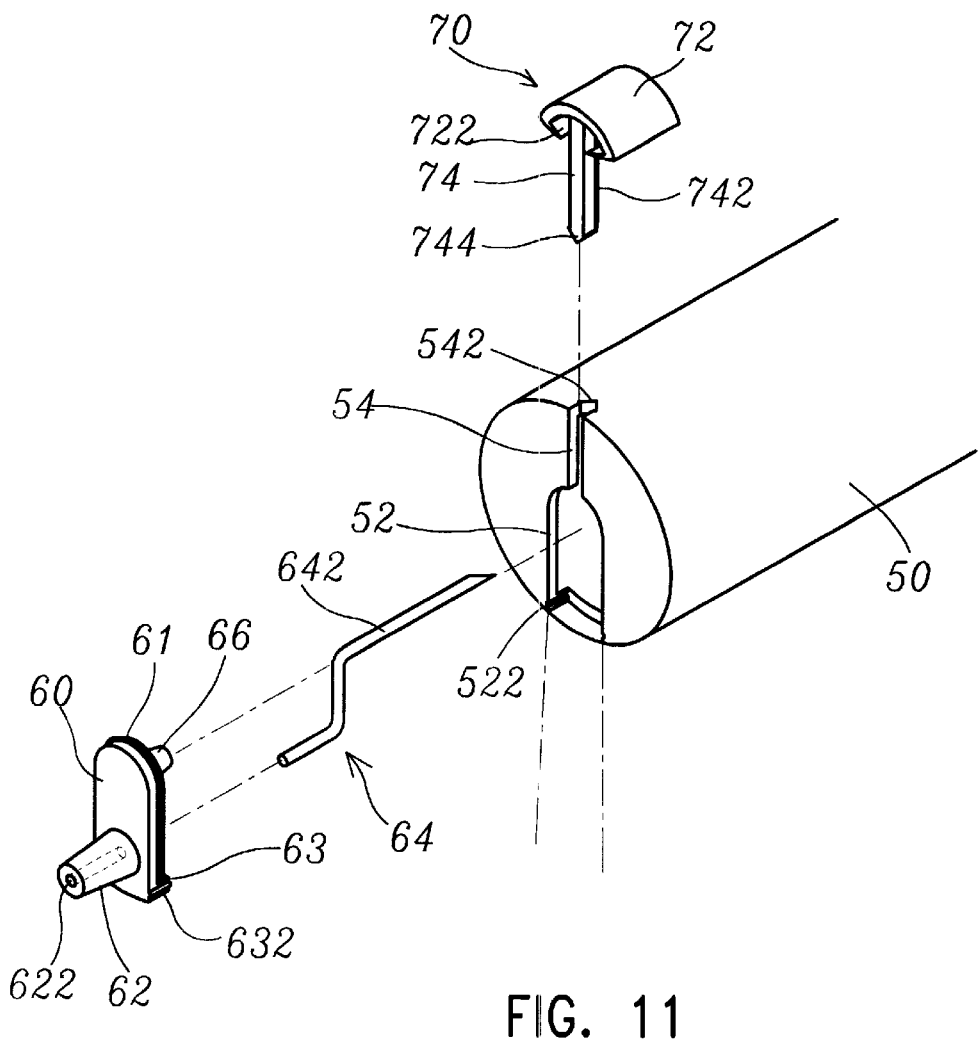
FIG. 11 is an explosive view of the front part of another preferred embodiment of the present invention.
Figure 12:
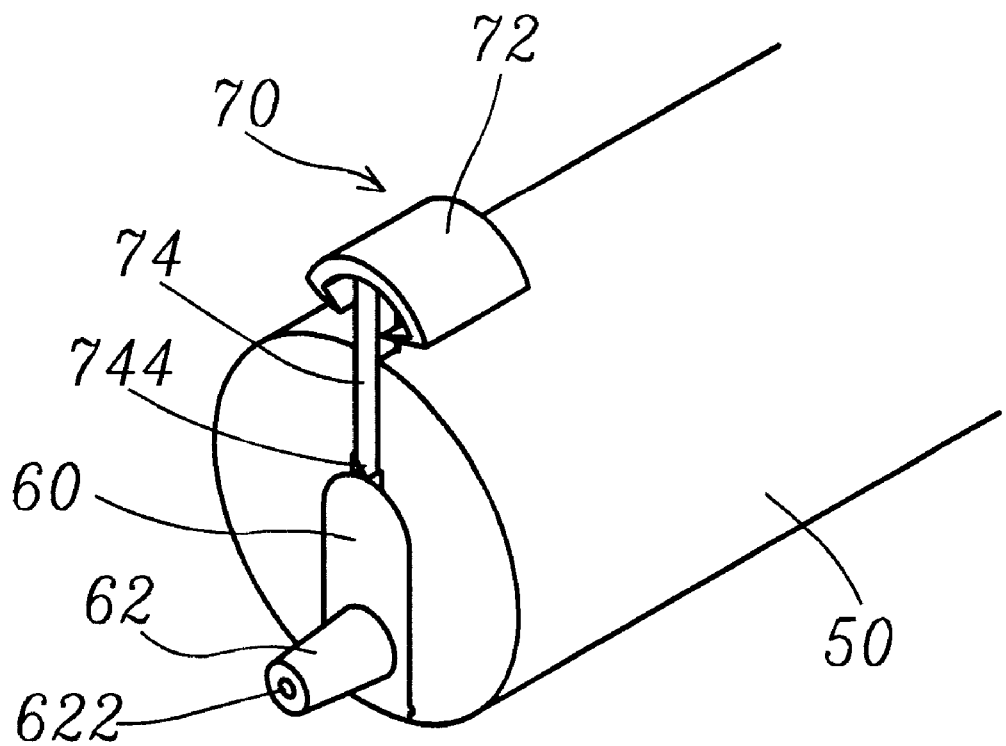
FIG. 12 is a perspective view of the front part of another preferred embodiment of the present invention.

Referring also to FIG. 8, a cannula needle can be located in the guiding hole 222 in advance when the eccentric reduced portion 22 of the reduced lining tube 20 is in production. Thus, there is no need to insert the needle separately, saving time and production cost.

FIGS. 9, 10, 11 and 12 show another preferred embodiment of the present invention comprising a hollow barrel 50, a directional sliding trench 52 transversely disposed at one side of the front end of the barrel 50, and a sliding slit 54 transversely disposed at another side opposite to the trench. A needle set 60 and a press plate 70 are further disposed in the trench 52 and the slit 54 respectively. An eccentric reduced portion 62 is still disposed on the upper surface of the needle seat, and a needle head 30 may be wedged on the eccentric reduced portion 62. A guiding hole is pierced through the eccentric reduced portion 62 so that a reversed Z-shaped needle 64 can be fixed therein and a lower needle tip 642 of the needle 64 can be placed at the central axial line of the reduced lining tube 50 firmly. A fixing seat 66 is disposed at the lower side of the needle seat 20 for receiving and fixing the needle 64 therein. Because the needle seat 60 can be fixed firmly in the trench 52, a positioning flange 61 is disposed around the outside profile of the needle seat 60, and a small flange 632 is attached to each flank side of a convex plate 63. A guiding groove 522 is disposed at each flank side of the trench corresponding to the position of the flange 632 so as to fix the flange therein to prevent the needle seat from dropping out of the trench. Moreover, in order to assemble the needle seat 60 easily into the tench 52, the trench 52 has a certain degree of angle between its two sides so that the width of the opening at the front edge is larger than the one of the end, enabling the needle seat 60 to easily slip into the trench 52. The press plate 70 has an end face 72 and a guiding stick 74, the guiding stick 74 has a triangle shape strip 742 at its flank side. The sliding slit 54 has a triangle shape slit opening 542 at its flank side corresponding to the position of the strip 742, so as to move the press plate 70 as a guide. A triangle shape inverted hook is formed at the end of the guiding stick 74 in order to be connected with the joint of the slit 54 and the trench 52 when the press plate 70 is positioned in the slit 54, enabling the press plate 70 not to slide backward to separate from the slit 54. An arc spring plate 722 is connected to the end of each flank side below the end face 72 to provide proper elastic force. A vacuum tube 40 is further disposed in the barrel 50, and an elastic plug 42 is firmly covered in the opening at the upper end of the vacuum tube 40, wherein the vacuum tube is available in the market.

Figure 13:
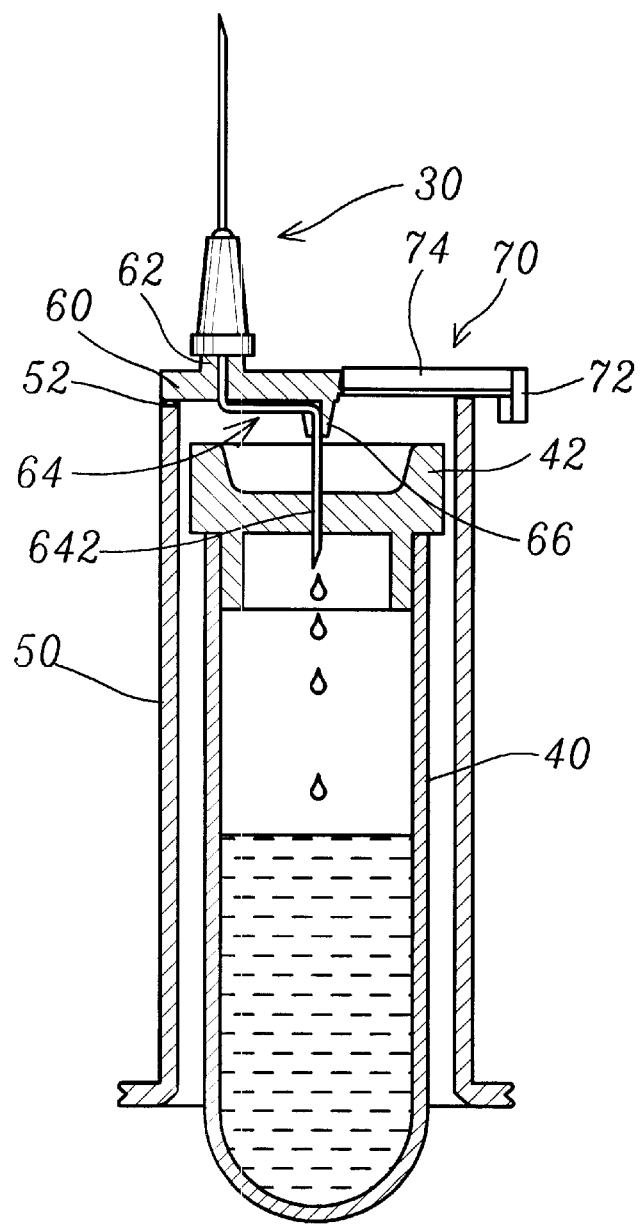
FIG. 13 is a longitudinal sectional view of another preferred embodiment of the present invention during use.
Figure 14:
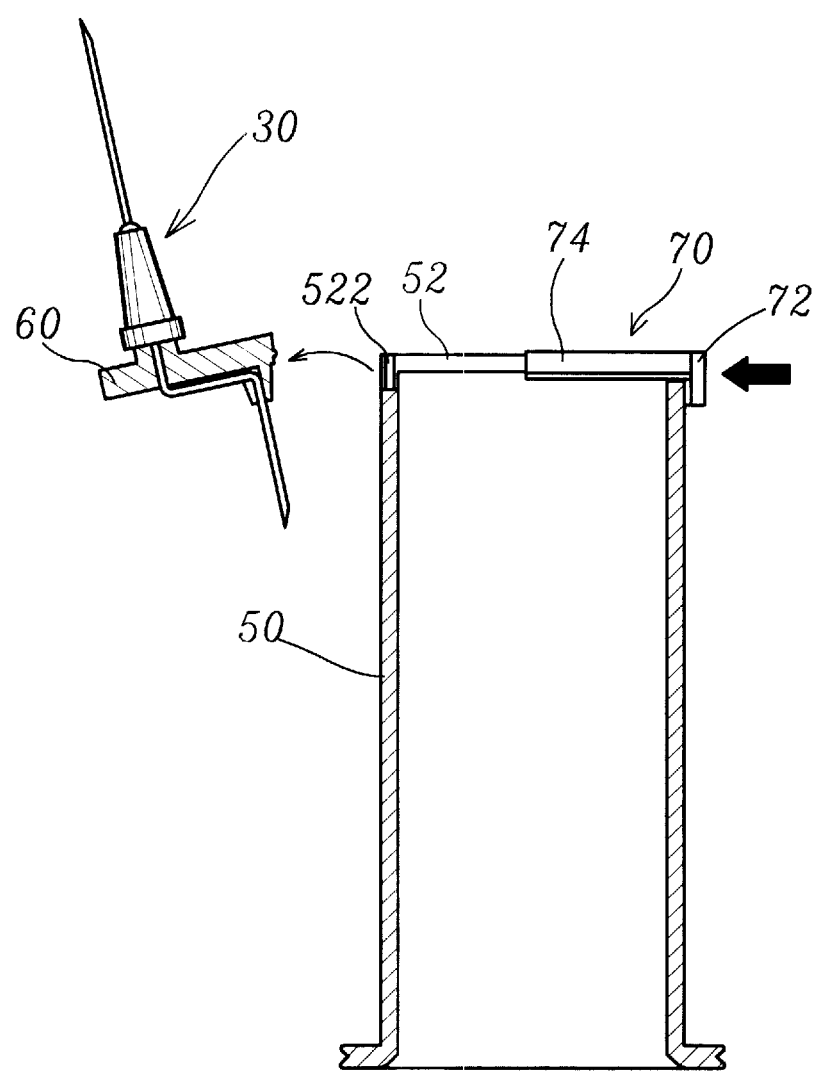
FIG. 14 is a schematic longitudinal sectional view of another preferred embodiment of the present invention, showing a needle seat being separated from a syringe; and, FIG. 15 is a schematic longitudinal sectional view of another preferred embodiment of the present invention, showing a needle seat being wedged into a syringe.
Figure 15:
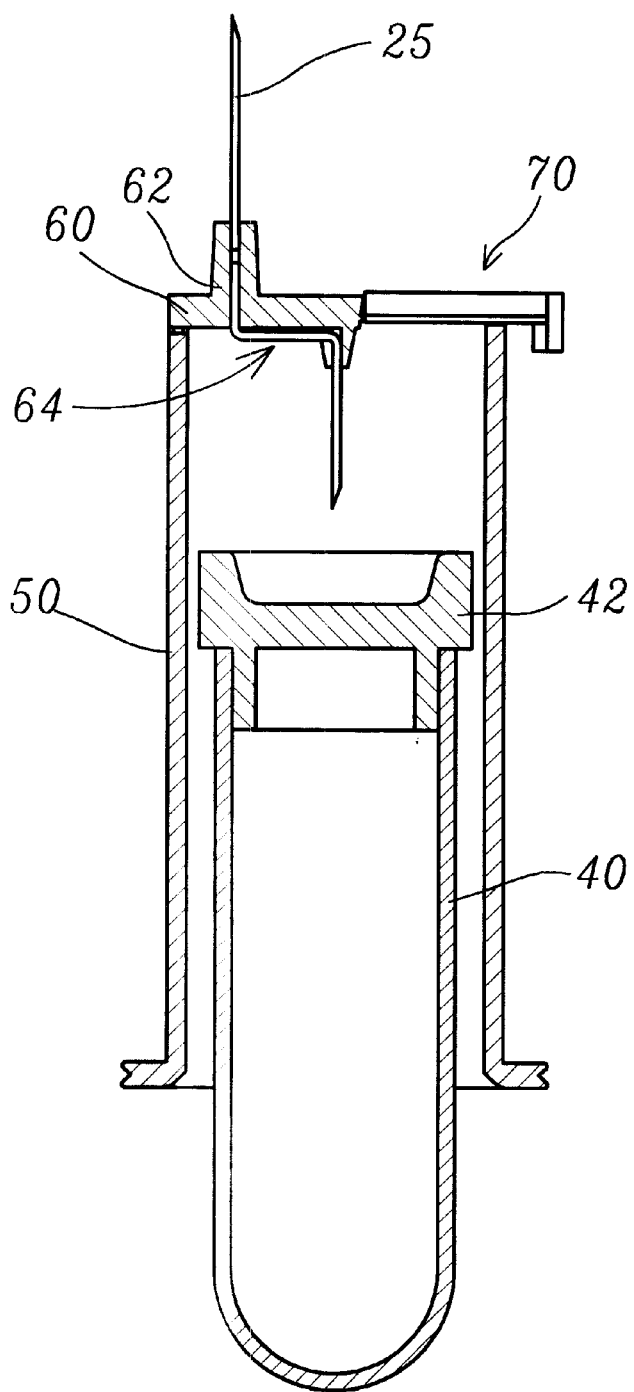

Next, referring to FIG. 13, when taking a blood sample, strike the needle head into the vein of a patient, then move the vacuum tube 40 toward the needle 64 inside the barrel 10 to allow the plug 42 of the cup 40 to be pierced. The blood from the vein of the patient will pass through the needle head 30, the guiding hole 622, the needle 64, and into the vacuum blood collecting cup 40. When the blood sampling is over, the press plate may be pushed 70 to separate the needle seat 60 from the trench. Place the needle in a needle head collector, and change the needle seat 60 and needle head for the next blood sampling to avoid the infection of virus.

The advantage of the invention is that a proper thickness needle head 30 may be chosen to wedge on the eccentric reduced portion 22, 62, and the needle head can be a conventional needle head instead of using a particular one that needs a new mold to produce saving costs. Moreover, since a conventional vacuum blood collecting cup can still be used after the needle head 30 is eccentrically disposed, the needle 26, 64 of the invention is designed to be reversed Z-shaped so as to position the lower needle tip 262, 642 of the needle 26, 64 at the center interior the barrel 10 and 50. Therefore, the lower needle tip 262, 642 can prick through the plug at the center, alleviating the need for a vacuum blood collecting cup.

It is to be understood that the drawing is designed for purpose of illustration only, and is not intended for use as a definition of the limits and scope of the invention disclosed.

What is claimed is:

1. An ergonomic safety vacuum syringe for sampling blood, comprising:

a vacuum tube;

a hollow barrel having an end surface and a cylindrical side surface, said hollow barrel having a reduced inlet formed through said end surface and having a guiding slit formed through said cylindrical side surface;

a reduced lining tube having an opening formed therethrough on a proximal end thereof and being mounted within said hollow barrel, said reduced lining tube having an eccentric reduced portion being formed on and projecting from a distal end thereof, said eccentric reduced portion being received within said reduced inlet, said eccentric reduced portion having a guiding hole formed therethrough, said reduced lining tube having a press plate formed thereon and projecting therefrom, said press plate being positioned within said guiding slit of said hollow barrel;

a first needle coupled to said eccentric reduced portion;

a second needle having a reverse Z-shape and opposing first and second ends, said first end being received within said guiding hole, said second end being positioned along a central axis of said reduced lining tube; and, a hook-shaped flange formed in an inner wall adjacent to said end surface of said hollow barrel to fix said reduced lining tube against downward slippage.

2. The ergonomic safety vacuum syringe for sampling blood as recited in claim 1, wherein said reduced lining tube has a fixing seat positioned at said central axis of said reduced lining tube to fix said second end of said second needle along said central axis.

3. The ergonomic safety vacuum syringe for sampling blood as recited in claim 1, wherein a plurality of small slits are formed through said reduced lining tube adjacent said proximal end to enable said proximal end of said reduced lining tube to maintain its elasticity.

4. The ergonomic safety vacuum syringe for sampling blood as recited in claim 1, wherein said eccentric reduced portion has a circular flange formed on an outer wall thereof and said reduced inlet has a circular groove formed in an inner surface thereof to receive said circular flange therein.

5. The ergonomic safety vacuum syringe for sampling blood as recited in claim 1, wherein said guiding slit has a stopping groove portion abutting a first portion of said guiding slit, said first portion of said guiding slit having a width smaller than a width of said stopping groove portion.

6. The ergonomic safety vacuum syringe for sampling blood as recited in claim 5, wherein said guiding slit includes a second portion with a plurality of bulging points disposed therein, said second portion being disposed proximal of said stopping groove portion.

7. The ergonomic safety vacuum syringe for sampling blood as recited in claim 1, wherein said first needle is a needle head releasably coupled to said eccentric reduced portion.

* * * * *